United States Patent [19]
Amselem

[11] 3,969,358
[45] July 13, 1976

[54] PROCESS FOR THE PREPARATION OF THIENO [3,2-C] PYRIDINE AND THIENO [2,3-C] PYRIDINE

[75] Inventor: Armand Amselem, Toulouse, France

[73] Assignee: Parcor, Paris, France

[22] Filed: June 25, 1975

[21] Appl. No.: 590,132

[30] Foreign Application Priority Data
July 16, 1974    France .............................. 74.24633

[52] U.S. Cl. ....................... 260/294.8 C; 260/329 S
[51] Int. Cl.$^2$ ...................................... C07D 213/28
[58] Field of Search ................... 260/294.8 C, 329 S

[56] References Cited
UNITED STATES PATENTS
3,655,681    4/1972    Nakanishi et al. ........... 260/294.8 C

*Primary Examiner*—Alan L. Rotman
*Attorney, Agent, or Firm*—Young & Thompson

[57] ABSTRACT

The present invention relates to a process for the preparation of thieno[3,2-c]pyridine or thieno[2,3-c]pyridine, comprising cyclizing a N-(3-thienyl)-methyl-N-[2,2-(OR)$_2$]ethyl-para-toluene sulfonamide or a N-(2-thienyl)-methyl-N-[2,2-(OR)$_2$]ethyl-para-toluene sulfonamide, respectively, in which R is lower alkyl or both R groups form together a 2- or 3-membered alkylene radical, by treatment with an acid in the presence of an inert organic solvent.

7 Claims, No Drawings

PROCESS FOR THE PREPARATION OF THIENO [3,2-C] PYRIDINE AND THIENO [2,3-C] PYRIDINE

This invention relates to a process for preparation of thieno[3,2-c]pyridine or thieno[2,3-c]pyridine which are known compounds already used as intermediates in the synthesis of a large number of derivatives used both in the chemical and pharmaceutical industries.

Said derivatives, which may be represented by the following structural formulae:

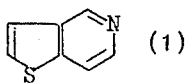 (1)   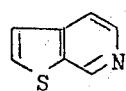 (1a)

have been studied by many authors and different syntheses have been described. However, the cost of such compounds is very high because all attempts to develop an inexpensive synthesis procedure providing good yields have heretofore failed.

Thus, L. H. Klemm, J. Shabtol, D. R. McCoy and W. K. Kiang (Heterocyclic Chem., 5, 883, 1968 and ibid. 6, 813, 1969) have described a synthesis via thermolysis of 1-benzylthio-2-(4-pyridyl)ethane at 600°C, with poor yields.

S. Gronowitz and E. Sandberg (Arkiv. Kemi., 32, 217, 1970 and ibid., 32, 249, 1970) conducted the synthesis of derivative (1) from 2-thiophene carboxaldehyde.

Therefore, the object of the present invention is to provide an inexpensive procedure for the ready synthesis of thieno [3,2-c]-pyridine or thieno [2,3-c]pyridine, in good yields.

The process according to the invention comprises cyclizing a N-(3-thienyl)-methyl-N-[2,2-(OR)₂]ethyl-para-toluene sulfonamide having the formula:

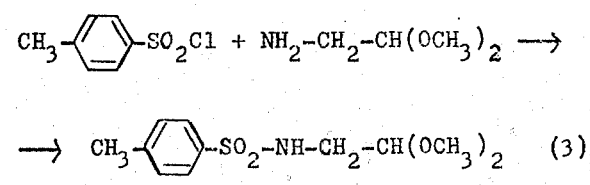 (2)

or a N-(2-thienyl)-methyl-N-[2,2-(OR)₂]ethyl-p-toluene sulfonamide having the formula:

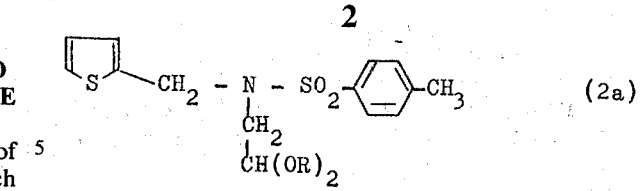 (2a)

in which R is a lower alkyl group or both R groups form together a 2- or 3-membered alkylene radical, by acid treatment in the presence of an organic solvent, to give derivative (1) or derivative (1a); respectively.

As acid, use can be made of a strong inorganic acid such as hydrochloric acid, sulfuric acid, hydrobromic acid, and the like.

The solvent used as reaction medium may be an inert organic solvent such as dioxane ethanol, isopropanol, butanol, and the like.

The temperature at which the cyclization should be carried out may vary from 50°C to the boiling temperature of the mixture.

The sulfonamide of the formula (2) may be prepared via two different routes which, for simplicity, are illustrated below only in the case of a radical R which is the methyl radical.

a. From 3-bromomethyl-thiophene

3-Bromomethyl-thiophene is reacted with N-(2,2-dimethoxy)-ethyl-para-toluene sulfonamide (Yield: 78%) which is itself obtained by condensation of the aminoacetaldehyde dimethyl acetal with para-toluenesulfonyl chloride (Yield: 95%), according to the following reaction scheme:

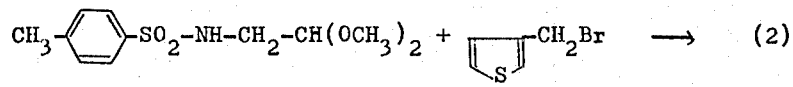

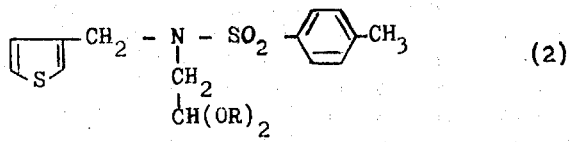 (3)

b. From 3-thienaldehyde

Para-Toluene sulfonyl chloride is reacted with N-(2,2-dimethoxy)-ethyl-(3-thienyl)methylamine (Yield: 84%) (4), itself obtained by reducing with sodium borohydride NaBH₄ the Schiff base formed between 3-thienaldehyde and the aminoacetaldehyde dimethyl acetal (Yield: 96%).

The reaction scheme is as follows:

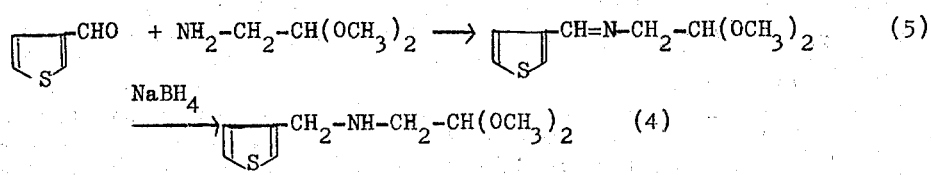

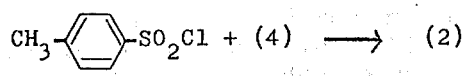

The sulfonamide of the formula (2a) may also be prepared by two different routes:

a. By reaction of 2-chloromethyl thiophene with N-(2,2-dimethoxy)-ethyl-p-toluene sulfonamide (3a) (Yield: 17%):

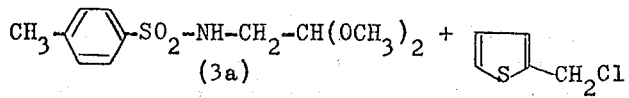  (2a)

b. By reaction of p-toluenesulfonyl chloride with N-(2,2-dimethoxy)-ethyl-(2thienyl)methylamine (in a yield of 84%):

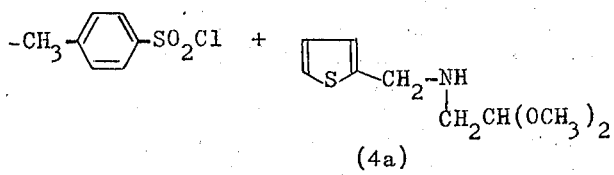  (2a)

Compound (4a) was obtained, in a yield of 71%, by reduction with NaBH₄ of the Schiff base formed between 2-thienaldehyde and the aminoacetaldehyde dimethylacetal (in a yield of 97%):

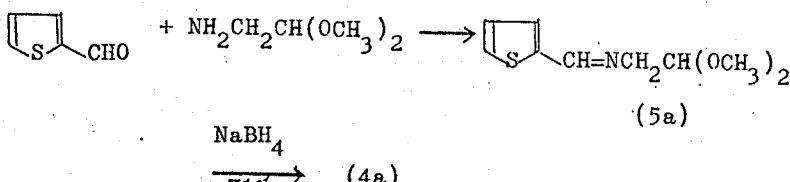

$$\xrightarrow{\text{NaBH}_4}_{71\%} \text{(4a)}$$

In both types of reactions, the aminoacetaldehyde dimethylacetal is used to constitute an intermediate derivative; however, one may without inconvenience use an acetal derived from a variety of alcohols, of the formula NH₂—CH₂—CH(OR)₂ in which CH(OR)₂ may represent, for example, CH(OC₂H₅)₂ or

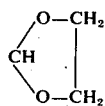

On the other hand, the conditions for the cyclization of compounds (2) and (2a) may be varied. One may either use different ratios of the components of the mixture, or replace ethanol by dioxane, isopropanol, butanol, and the like. HCl may be replaced by another strong mineral acid such as BHr or H₂SO₄. The reaction temperature may vary from 50°C to the boiling temperature of the mixture.

The following examples are given to illustrate the invention.

EXAMPLE 1

Preparation of thieno[3,2-c]pyridine a. From 3-bromomethyl-thiophene

A solution of 19 g (0.1 mole) para-toluene sulfonyl chloride in 100 ml chloroform is added dropwise to a vigorously stirred mixture comprising 10.5 g (0.1 mole) aminoacetaldehyde dimethylacetal, 10.5 g sodium carbonate, 100 ml chloroform and 50 ml water. The mixture is stirred during 6 hours at room temperature, after which the chloroform phase is separated, washed with water and dried over sodium sulfate to give, after evaporation of the solvent, 24 g of clear oil (Yield: 95.6%) comprising the sulfonamide of the formula (3) which is used without further purification in the subsequent step.

A mixture containing 42.5 g of the sulfonamide of the formula (3) obtained above (0.164 mole), 30.5 g (0.175 mole) 3-bromomethyl -thiophene, 45 g anhydrous potassium carbonate and 250 ml dry ethanol is refluxed during 2.5 hours. After filtration, the solution is evaporated and the residue is taken up into isopropyl ether, to give 45.5 g (Yield: 78%) of a crystalline mass comprising the sulfonamide of the formula (2).

b. From 3-thienaldehyde

Into a flask provided with a Dean-Stark water-separator and an ascending cooler are added 22.4 g (0.2 mole) 3-thienaldehyde, 23.1 g (0.2 mole) aminoacetaldehyde dimethyl acetal and 45 ml benzene. The mixture is refluxed until the theoretical amount of water formed in the reaction has been collected. Evaporation of the benzene and distillation of the residual oil give 38.2 g of the Schiff base of the formula (5) (Yield: 96%. B.p./0.1 mm Hg = 86°–90°C).

43.8 g (0.2 mole) of the compound of the formula (5) are dissolved in 185 ml ethanol and 12.5 g (0.33 mole) sodium borohydride NaBH₄ are added portionwise to the resulting solution. The mixture is left aside during one hour at room temperature and is then refluxed during one hour. The alcohol is evaporated in vacuo and the residue is taken up into 250 ml of 20% aqueous acetic acid solution. The resulting solution is washed with ether and is then made alkaline by addition of ammonia, after which it is re-extracted with ether. The ether fractions are combined, dried over sodium sulfate and concentrated in vacuo, to give 31.4 g (Yield: 71%) of an oily residue consisting of the amino compound of the formula (4).

A solution of 57.15 g (0.3 mole) paratoluene sulfonyl chloride in 400 ml chloroform is added dropwise to a vigorously stirred mixture comprising 61 g (0.3 mole) of the previously obtained compound (4), 31.8 g sodium carbonate, 400 ml chloroform and 250 ml water. The mixture is then stirred during a further 4 hours at room temperature, after which the chloroform fraction is separated, washed with water, dried over sodium sulfate and evaporated. The oily residue, which rapidly sets to a mass, is recrystallized from a mixture of 200 ml isopropyl ether and 30 ml isopropanol. Filtration of the resulting material provides 89.5 g (Yield: 84%) of the sulfonamide of the formula (2).

c. Preparation of thieno[3,2-c]pyridine 25 g of the sulfonamide of the formula (2) obtained either from 3-bromomethyl-thiophene or from 3-thienaldehyde are mixed with 80 ml 12N HCl and 500 ml dioxane and the resulting mixture is then refluxed during 4 hours.

After cooling, the mixture is concentrated in vacuo and the residue is taken up into water.

The aqueous solution is then extracted with ether, after which it is made alkaline by addition of dilute sodium hydroxide and then re-extracted with methylene chloride.

The organic phases are combined, dried over sodium sulfate and evaporated in vacuo. The resulting oily residue is then distilled under reduced pressure, to give 6.7 g thieno[3,2-c]-pyridine between 57°C and 60°C, under a pressure of 0.1 mm Hg.

EXAMPLE 2

Preparation of thieno[2,3-c]pyridine a. From 2-chloromethyl-thiophene

A mixture of 20 g (0.15 mole) 2-chloromethyl thiophene, 37 g (0.143 mole) sulfonamide (3a), 40 g anhydrous potassium carbonate and 200 ml dry ethanol is refluxed during 12 hours. After filtration, the solution is evaporated and the residue is dissolved in diethyl ether. The solution is washed with dilute sodium hydroxide (2N NaOH) and then with water. It is then dried over sodium sulfate and evaporated. The residue is taken up into isopropyl ether and the resulting crystalline mass is then filtered, to give 8.8 g (Yield: 17%) of compound (2a), m.p. 84°C.

b. From 2-thienaldehyde

Into a flask provided with a Dean-Stark water-separator and an ascending cooler are added 448.6 g (4 moles) 2-thienaldehyde, 462.5 g (4.4 moles) aminoacetaldehyde dimethylacetal and 800 ml benzene. The mixture is refluxed until the theoretical amount of water formed in the reaction has been separated. After evaporation of the benzene, the residual oil, consisting of the Schiff base (5a) is distilled under reduced pressure (b.p. 110°C. Yield: 784 g; 97%).

To a solution of 299 g of compound (5a) in 1100 ml ethanol are added portionwise 87.15 g NaBH$_4$. The mixture is left aside at room temperature during one hour and is then refluxed during 3 hours. The alcohol is evaporated in vacuo and the residue is taken up into 1000 ml of 20% aqueous acetic acid solution. The resulting solution is washed with ether, then made alkaline by addition of ammonia and re-extracted with methylene chloride. The organic fractions are combined, dried over sodium sulfate and concentrated in vacuo. The oily residue, consisting of compound (4a) is distilled under reduced pressure (b.p.$_{0.5}$: 95°C. Yield: 217 g; 71%).

A solution of 203.8 g (1.07 mole) p-toluenesulfonyl chloride in 500 ml chloroform is added dropwise to a vigorously stirred solution comprising 217 g (1.07 mole) amine (4a), 113.4 g sodium carbonate, 2000 ml chloroform and 600 ml water. The mixture is maintained 8 hours at room temperature, with stirring, after which the chloroform fraction is separated, washed with water, dried over sodium sulfate and evaporated. The oily residue sets rapidly to a mass and is recrystallized from a mixture of 400 ml isopropyl ether and 50 ml isopropanol, to give 363 g (Yield: 95%) of tosylated compound (2a), m.p. 84°C.

c. Preparation of thieno[2,3-c]pyridine

A mixture of 128.8 g of sulfonamide (2a) obtained according to any one of the above procedures, 630 ml 12N HCl and 630 ml ethanol is refluxed during 4 hours. After cooling, the mixture is concentrated in vacuo and the residue is taken up into water.

The aqueous solution is then made alkaline by addition of ammonia and extracted with methylene chloride. The organic phases are combined, dried over sodium sulfate and evaporated in vacuo. The oily residue is then distilled under reduced pressure, to give 37 g (Yield: 76%) of thieno-pyridine (1a) at 87°C/1 mm Hg.

Having now described my invention what I claim as new and desire to secure by Letters Patent is:

1. Process for the preparation of a compound selected from the group consisting of thieno[3,2-c]pyridine and thieno [2,3-c]-pyridine, comprising cyclizing a compound selected from the group consisting of a N-(3,thienyl)methyl-N-[2,2-(OR)$_2$]ethyl-para-toluene sulfonamide and a N-(2-thienyl)-methyl-N-[2,2-(OR)$_2$]-ethyl-para-toluene sulfonamide, respectively, in which the radicals R, when taken individually, are lower alkyls and, when taken together in (OR)$_2$, may also form a group selected from the 2- and 3-membered alkylene groups, by treatment with a strong mineral acid in the presence of an inert organic solvent at a temperature between about 50°C and the boiling temperature of the mixture.

2. Process as claimed in claim 1, wherein the strong mineral acid is selected from the group consisting of hydrochloric, hydrobromic and sulfuric acids.

3. Process as claimed in claim 1, wherein the inert organic solvent is selected from the group consisting of dioxane, ethanol, isopropanol and butanol.

4. Process for the preparation of thieno[3,2-c]-pyridine which comprises the steps of:
    1. reacting 3-bromomethyl-thiophene with N-[2,2-(OR)$_2$]-ethyl-para-toluene sulfonamide, in which the radicals R, when taken individually, are lower alkyls and when taken together in (OR)$_2$, may also form a group selected from the 2- and 3-membered alkylene groups, in the presence of ethanol under reflux to obtain N-(3-thienyl)- methyl-N-[2,2-(OR)$_2$]-ethyl-para-toluene sulfonamide;
    2. cyclizing the resulting compound by treatment with a strong mineral acid in the presence of an inert solvent at a temperature between about 50°C and the boiling temperature of the mixture.

5. Process for the preparation of thieno[3,2-c]-pyridine which comprises the steps of:
    1. reacting 3-thienaldehyde with a compound of formula NH$_2$—CH$_2$—CH(OR)$_2$, in which the radicals R, when taken individually, are lower alkyls and when taken together in (OR)$_2$ may also form a group selected from the 2- and 3-membered alkylene groups, in the presence of benzene under reflux to give the corresponding Schiff base;
    2. reducing said Schiff base with sodium borohydride in the presence of ethanol first at room temperature and then under reflux to obtain N-[2,2-(OR)$_2$]-ethyl-(3-thienyl)-methylamine;
    3. reacting the compound obtained in step 2 with para-toluene sulfonyl chloride in the presence of chloroform and water at room temperature under stirring to obtain N-(3-thienyl)-methyl-N-[2,2-(OR)$_2$]-ethyl-para-toluene sulfonamide;
4. cyclizing the resulting compound by treatment with a strong mineral acid in the presence of an inert solvent at a temperature between about 50°C and the boiling temperature of the mixture.

6. Process for the preparation of thieno[2,3-c]-pyridine which comprises the steps of:
   1. reacting 2-chloromethyl-thiophene with N-[2,2-(OR)$_2$]-ethyl-para-toluene sulfonamide, in which the radicals R, when taken individually, are lower alkyls and when taken together in (OR)$_2$, may also form a group selected from the 2- and 3-membered alkylene groups, in the presence of ethanol under reflux to obtain N-(2-thienyl)-methyl-N-[2,2-(OR)$_2$]-ethyl-para-toluene sulfonamide;
   2. cyclizing the resulting compound by treatment with a strong mineral acid in the presence of an inert solvent at a temperature between about 50°C and the boiling temperature of the mixture.

7. Process for the preparation of thieno[-2,3-c]-pyridine which comprises the steps of:
   1. reacting 2-thienaldehyde with a compound of formula NH$_2$—CH$_2$—CH(OR)$_2$, in which the radicals R, when taken individually, are lower alkyls and when taken together in (OR)$_2$ may also form a group selected from the 2- and 3-membered alkylene groups, in the presence of benzene under reflux to give the corresponding Schiff base;
   2. reducing said Schiff base with sodium borohydride in the presence of ethanol first at room temperature and then under reflux to obtain N-[2,2-(OR)$_2$]-ethyl-(2-thienyl)-methylamine;
   3. reacting the compound obtained in step 2 with para-toluene sulfonyl chloride in the presence of chloroform and water at room temperature under stirring to obtain N-(2-thienyl)-methyl-N-[2,2-(OR)$_2$]-ethyl-para-toluene sulfonamide;
   4. cyclizing the resulting compound by treatment with a strong mineral acid in the presence of an inert solvent at a temperature between about 50°C and the boiling temperature of the mixture.

* * * * *